United States Patent
Ishida

(12) 
(10) Patent No.: US 6,618,136 B1
(45) Date of Patent: Sep. 9, 2003

(54) METHOD AND APPARATUS FOR VISUALLY INSPECTING TRANSPARENT BODY AND TRANSLUCENT BODY

(75) Inventor: Futoshi Ishida, Takatsuki (JP)

(73) Assignee: Minolta Co., Ltd., Osaka (JP)

( * ) Notice: Subject to any disclaimer, the term of this patent is extended or adjusted under 35 U.S.C. 154(b) by 0 days.

(21) Appl. No.: 09/390,690

(22) Filed: Sep. 7, 1999

Related U.S. Application Data
(60) Provisional application No. 60/128,283, filed on Apr. 8, 1999.

(30) Foreign Application Priority Data

Sep. 7, 1998 (JP) .......................................... 10-252357

(51) Int. Cl.[7] .............................................. G01N 21/88
(52) U.S. Cl. ................................ 356/239.1; 356/239.7; 356/239.8
(58) Field of Search .......................... 356/239.1, 239.2, 356/239.7, 239.8, 124, 445; 250/559.11, 559.45

(56) References Cited

U.S. PATENT DOCUMENTS

| | | | | | |
|---|---|---|---|---|---|
| 3,814,946 A | * | 6/1974 | Takahashi et al. | ....... | 356/239.7 |
| 5,331,396 A | * | 7/1994 | Yukawa et al. | .......... | 356/237.4 |
| 5,539,514 A | * | 7/1996 | Shishido et al. | ......... | 356/237.5 |
| 5,892,579 A | * | 4/1999 | Elyasaf et al. | ........... | 356/239.8 |

* cited by examiner

*Primary Examiner*—Zandra V. Smith
(74) *Attorney, Agent, or Firm*—McDermott, Will & Emery

(57) ABSTRACT

A system and method of visually inspecting a transparent body and a translucent body comprises applying light to a reverse surface of an object to be inspected by a transmission light source, and applying light, at a low angle, to at least one of an obverse surface and the reverse surface of the object to be inspected by a reflection light source. Concave defects and adherents of the object to be inspected are detected by use of transmitted light emitted from the transmission light source, and adherents of the object to be inspected are detected by use of reflected scattered light emitted from the reflection light source.

20 Claims, 4 Drawing Sheets

METHOD AND APPARATUS FOR VISUALLY INSPECTING TRANSPARENT BODY AND TRANSLUCENT BODY

This application claims the benefit of application Ser. No. 60/128,283 filed Apr. 8, 1999.

This application is based on application No. 10-25235, filed in Japan, the contents of which are hereby incorporated by reference.

BACKGROUND OF THE INVENTION

1. Technical Field of the Invention

The present invention relates to a method and an apparatus for visually inspecting a transparent body and a translucent body such as a glass hard disk substrate, an LCD substrate or a lens. More particularly, the present invention relates to a method and an apparatus for visual inspection in which scratches or pits which are concave defects and particles which are adherents are detected so as to be distinguished from each other.

2. Prior Art

As a conventional visual inspection method for inspecting concave defects and adherents of an object to be inspected, Japanese Laid-open Patent Application No. Sho 60-219542 discloses a method in which, using the fact that p-polarized components are included in light scattered from foreign substances, adherents on a wafer are detected by detecting p-polarized components included in scattered light by applying s-polarized laser light onto the surface of the wafer at a low angle. This method is for opaque bodies having a high surface reflectance such as wafers, and resolution is not high for transparent bodies and translucent bodies.

Japanese Laid-open Patent Application No. Hei 1-96537 discloses a method in which a laser beam is applied to the surface of a glass disk in a vertical direction, and light scattered from protruding defects existing on the glass disk is detected by a low-angle light receiver and scattered light reflected from concave defects on the glass disk to converge is extracted by a half mirror and received.

Japanese Laid-open Patent Application No. Hei 5-52764 discloses a method in which obliquely incident light is applied to a glass substrate and is received at two points of a high angle and a low angle as first detection light and second detection light, and discrimination between concave defects and adherents on the glass substrate is performed based on the intensity of the p-polarized components in the first detection light and the ratio of the intensity of the second detection light to the intensity of detection light of a first detection component.

Japanese Laid-open Patent Application No. Hei 6-138045 discloses a method in which detection light is applied to the surface of a glass substrate in a vertical direction and light scattered from fine particles existing on the obverse and the reverse surfaces of the substrate is detected by a detector disposed within the vicinity of the critical angle of total reflection of the substrate on the obverse surface of the substrate.

Japanese Laid-open Patent Application No. Hei 6-222013 discloses a method in which scratches and small particles are detected by the dark-field reflection image of a first light beam of a low incidence angle, stains are detected by the bright-field reflection image of a scattered second light beam, and pits and bulges are detected by the bright-field reflection image of a third light beam of a high incidence angle.

These methods all use reflection light and are effective in detecting adherents. However, when the object to be inspected is a transparent or a translucent body, these methods are unsuitable for detecting concave defects because contrast cannot be obtained.

As a method using transmitted light, Japanese Laid-open Patent Application No. Hei 7-225198 discloses a method in which laser light is applied to a glass substrate, and adherents are detected by a sensor disposed on the optical path of the transmitted light and concave defects are detected by a sensor disposed in a position off the optical path of the transmitted light. However, in the method using only transmitted light, not only adherents but also concave defects are simultaneously detected, so that it is difficult to distinguish concave defects from adherents.

BRIEF DESCRIPTION OF THE INVENTION

Problems to be Solved by the Invention

The present invention is made in view of the above-described problems, and an object thereof is to provide a method and an apparatus for visually inspecting a transparent body and a translucent body in which concave defects and adherents are distinguished from each other and highly sensitive detection can be performed for both.

Solutions to the Problems Provided by the Invention

To solve the above-described problems, in the method of visually inspecting a transparent body and a translucent body according to the present invention, light is applied to a reverse surface of an object to be inspected by a transmission light source, light is applied, at a low angle, to at least one of an obverse surface and the reverse surface of the object to be inspected by a reflection light source, and detection of concave defects and adherents of the object to be inspected by use of transmitted light emitted from the transmission light source and transmitted by the object to be inspected and detection of adherents of the object to be inspected by use of reflected scattered light emitted from the reflection light source and irregularly reflected at the object to be inspected are performed by a detector disposed on an obverse surface side of the object to be inspected in a position substantially parallel to an optical path of the transmission light source and where light from the transmission light source is not directly incident.

According to this method of the present invention, since concave defects and adherents of the object to be inspected are detected by use of transmitted light emitted from the transmission light source and transmitted by the object to be inspected and adherents of the object to be inspected is detected by use of reflected scattered light emitted from the reflection light source and irregularly reflected at the object to be inspected, concave defects and adherents can be inspected so as to be distinguished from each other. That is, by identifying the positions of concave defects and adherents by use of the transmission light source and then detecting adherents by use of the reflection light source, concave defects can be distinguished from adherents. Although the detection by use of the reflection light source is dark-field illumination and slightly low in contrast, since the positions of the defects are previously identified by the detection by use of the transmission light source, it is necessary only to determine whether the defect at each position is an adherent or not. Thus, the defect of low contrast can be made up for.

At the time of the detection by use of the reflection light source, scattering due to adherents on the object to be inspected is dominant, so that only the adherents can effectively be detected. Moreover, since the detector is disposed in a position not affected by total reflection, detection can be performed with high sensitivity. At the time of the detection by use of the transmission light source, since the detector is disposed in a position where light from the transmission light source is not directly incident although being close to bright-field illumination, a dark-field image with excellent contrast is obtained, so that concave defects and adherents can clearly be detected.

According to the method of the present invention, the concave defects and the adherents of the object to be inspected may be distinguished from each other by illuminating the object to be inspected with a combination of turning on and off of the transmission light source and the reflection light source and separately performing the detection of the concave defects and the adherents by use of the transmission light source and the detection of the adherents by use of the reflection light source. By doing so, the detection of concave defects and adherents by use of the transmission light source and the detection of adherents by use of the reflection light source can more clearly be performed. In this case, it is preferable to perform the detection of adherents by use of the reflection light source for both of the obverse and the reverse surfaces by turning the object to be inspected from side to side. Thereby, the adherents on the obverse and the reverse surfaces can be distinguished from each other.

Moreover, according to the method of the present invention, the reflection light source may be disposed on each of the obverse surface side and the reverse surface side of the object to be inspected, and the concave defects and the adherents of the object to be inspected may be distinguished from each other by illuminating the object to be inspected with a combination of turning on and off of the transmission light source and the two reflection light sources and separately performing the detection of the concave defects and the adherents by use of the transmission light source, detection of adherents on the obverse surface by use of the first reflection light source and detection of adherents on the reverse surface by use of the second reflection light source. By doing so, the adherents on the obverse and the reverse surfaces can be distinguished from each other without the object to be inspected being turned from side to side.

To solve the above-mentioned problems, the apparatus for visually inspecting a transparent body and a translucent body according to the present invention comprises:

a transmission light source disposed on a reverse surface side of an object to be inspected and applying light to a reverse surface of the object to be inspected;

a reflection light source disposed on at least one of an obverse surface side and the reverse surface side of the object to be inspected and applying light to the object to be inspected at a low angle; and a detector disposed on the obverse surface side of the object to be inspected in a position substantially parallel to an optical path of the transmission light source and where the light from the transmission light source is not directly incident, detecting concave defects and adherents of the object to be inspected by use of transmitted light emitted from the transmission light source and transmitted by the object to be inspected, and detecting adherents of the object to be inspected by use of reflected scattered light emitted from the reflection light source and irregularly reflected at the object to be inspected.

By performing a visual inspection of a transparent body and a translucent body by use of this apparatus, concave defects and adherents can be inspected so as to be distinguished from each other as described above.

In the apparatus of the present invention, it is preferable that an angle of inclination of the detector from the optical path of the transmission light source be 5±3 degrees. Moreover, it is preferable that an angle of incidence of the reflection light source on the object to be inspected be approximately 4±3 degrees.

Moreover, in the apparatus of the present invention, a light intercepting plate for preventing the light from the transmission light source from being directly incident on the detector can be disposed between the transmission light source and the object to be inspected or between the object to be inspected and the detector. By doing so, light from the transmission light source is not directly incident on the detector, so that resolution improves.

Further, in the apparatus of the present invention, it is preferable that the transmission light source be a light source in which angles of light beams illuminating the object to be inspected are substantially the same. With this, the scattered light can be made incident on the detector without any loss.

Other objects, features, and advantages of the invention will become apparent from the following description and from the claims.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE PRESENT INVENTION

Preferred Embodiments of the Invention

Hereinafter, embodiments of the present invention will be described with reference to the drawings.

First Embodiment

Figure 1A:
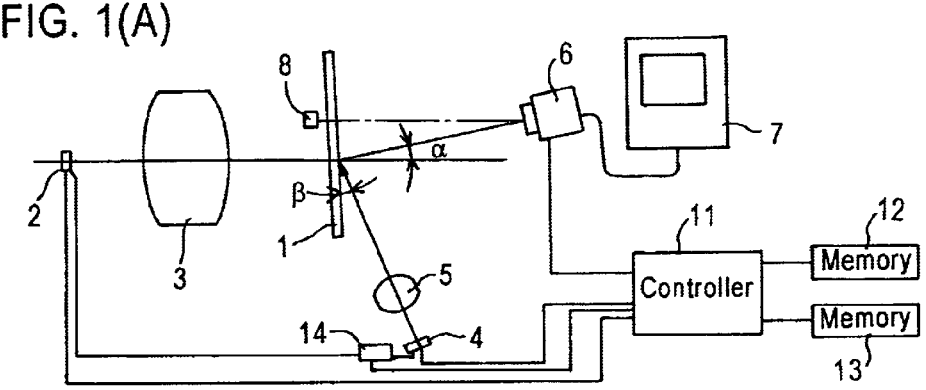
FIGS. 1A, 1B, and 1C are views showing a first embodiment of an apparatus for visually inspecting a transparent or a translucent body according to the present invention.

FIG. 1 A shows a first embodiment of an apparatus for visually inspecting a transparent or a translucent body according to the present invention.

The visual inspection apparatus comprises a transmission light source 2 and an optical system 3 that are disposed on one side of an object to be inspected 1 and a reflection light source 4, an optical system 5, a detector 6, a monitor 7, a controller 11, the controller having a memory 12 and a memory 13, and a switch 14, that are disposed on the other side of the object to be inspected 1. The controller 11 controls: activation of light sources 2 and 4; activation of switch 14; splitting of the detected signal from detector 6 to both the monitor 7 and the memory 12; and comparison of the detected images $I_1$ and $I_2$ by means of a comparator. The switch 14 may be any switch that controls light from the light sources, for example mechanical diaphragms or optical modulators. Although in some embodiments of the present invention, the controller 11 may directly control activation of the light sources 2 and 4, in other embodiments this control may be accomplished via the switch 14. Memory 12 stores detected image data, and may be for example a random access memory. Memory 13, which may be for example a read-only memory (ROM), stores system operation instructions for use by the controller 11. Memory 12 also functions as a work area for the system operation. Hereinafter, the detector 6 side surface of the object to be inspected 1 will be referred to as the obverse surface, and the transmission light source 2 side surface thereof, as the reverse surface.

The transmission light source 2 has its optical path disposed on the reverse surface of the object to be inspected 1 and is capable of illuminating the object to be inspected 1 through the optical system 3. The transmission light source 2 comprises a halogen lamp and a light guide and has an aperture of approximately 4 mm. As the optical system 3, a condenser lens system with an aperture of 50 mm and a focal length of 80 mm is used. The distance between the optical system 3 and the object to be inspected 1 is 280 mm. The distance between the transmission light source 2 and the optical system 3 is adjusted so that the illuminated part on the object to be inspected 1 is approximately 50 mm. The luminance of the illuminated part is approximately 200 lx.

The reflection light source 4 has its optical path disposed so as to intersect the obverse surface of the object to be inspected 1 at a low angle and is capable of illuminating the object to be inspected 1 through the optical system 5. In this embodiment, the angle is approximately 2 degrees. The reflection light source 4 comprises a halogen lamp and a light guide, and as the light source 4, one is used that has a linear configuration of approximately 1 mm×50 mm extending in a direction vertical to the plane of the figure. As the optical system 5, a cylindrical lens system with a length of 50 mm is used. The distance between the optical system 5 and the object to be inspected 1 is approximately 100 mm. The luminance of the illuminated part is approximately 180 lx.

Switching between the transmission light source 2 and the reflection light source 4 as generally indicated by switch 14, can be performed, for example, by a non-illustrated shutter mechanism.

While the detector 6 is substantially parallel to the optical path of the transmitted light of the transmission light source 2, in order to prevent the transmitted light from being directly incident, the detector 6 is disposed so as to be inclined at an angle a to the optical path and a light intercepting plate 8 is disposed on a line passing through the detector 6 and being parallel to the optical path. The light intercepting plate 8 may be disposed between the objet to be inspected 1 and the detector 6 instead of being disposed between the transmission light source 2 and the object to be inspected 1 as shown in the figure. It is preferable that the angle of the inclination of the detector from the optical path of the transmission light source be 5±3. In this embodiment, the angle α is approximately 5 degrees. The detector 6 detects transmitted light from the transmission light source 2 and reflected scattered light from the reflection light source 4, and as the detector 6, for example, a CCD camera (sensor system ⅔ inch, 410 thousand pixels) may be used. The monitor 7 detects the detects the detection signal of the detector 6 by a non-illustrated image processor to display the image of the objet to be inspected 1.

Figure 3:
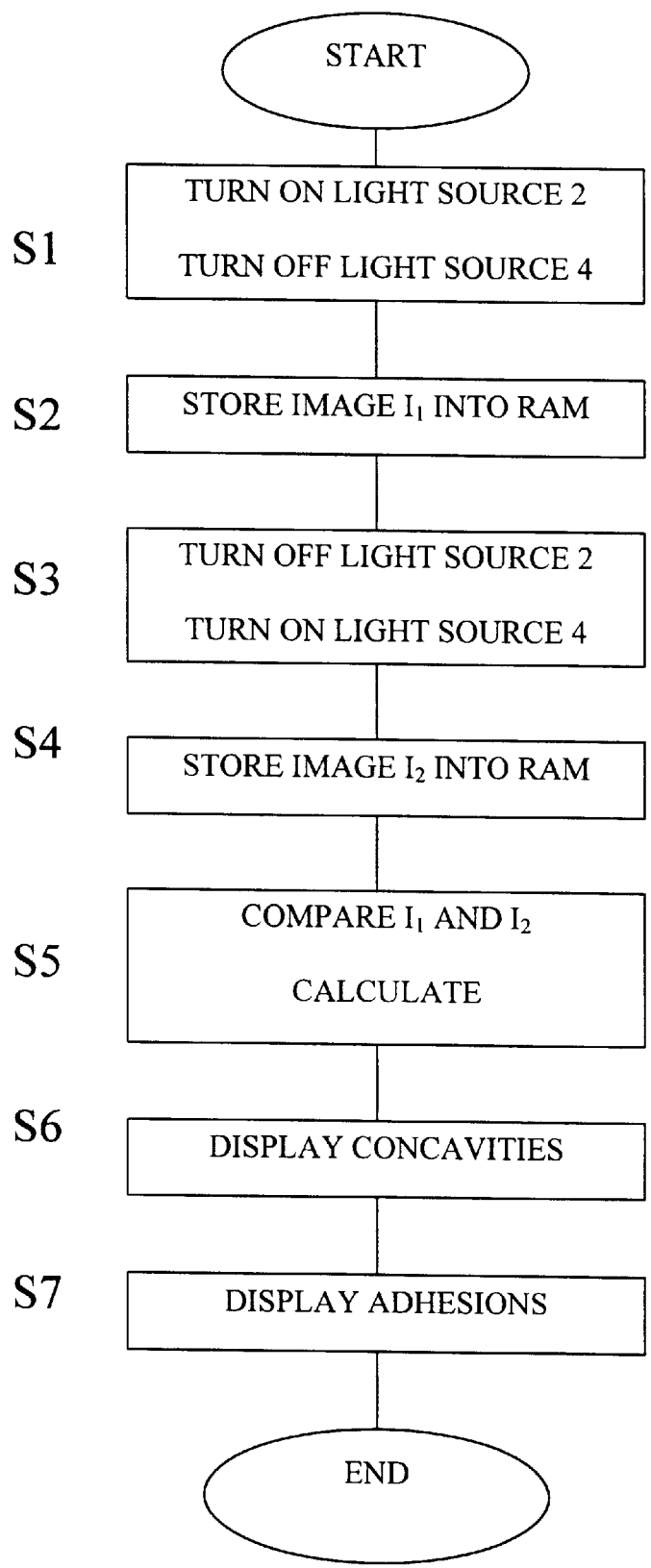
FIG. 3 is a method step diagram showing steps of operation of a first embodiment of an apparatus for visually inspecting a transparent or a translucent body according to the present invention.

Subsequently, a method of visually inspecting the object to be inspected 1 by using the visual inspection apparatus having the above-described structure will be described with reference to FIG. 1B, FIG. 1C, both with reference to FIG. 3. Here, a transparent glass substrate with a thickness of 1 mm is used as the object to be inspected 1, and concave defects and adherents thereof are detected so as to be distinguished from each other.

Figure 1B:
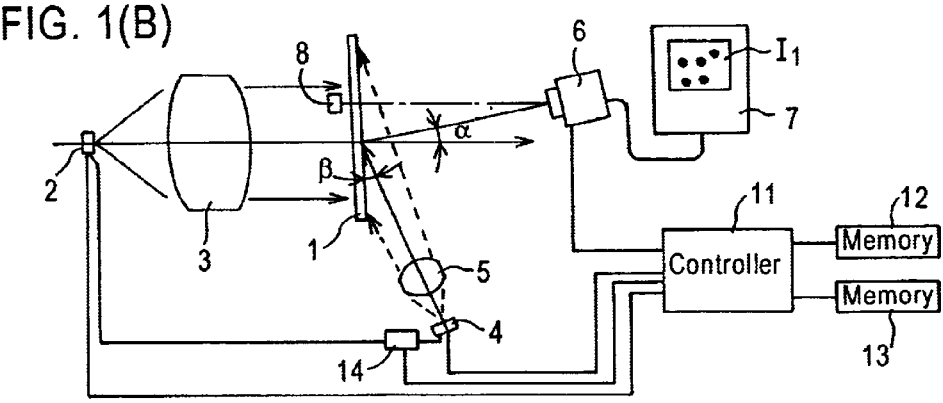

First, as shown in FIG. 1B, when the controller 11 instructs the switch, 14, which then turns off or blocks reflection light source 4, the object to be detected 1 is illuminated by the transmission light source 2 (S1). Then, the transmitted light transmitted by the object to be inspected 1 is detected by the detector 6 and is then concurrently displayed on the monitor 7 (image $I_1$) and stored in memory 12, for example, a random access memory, within the controller 11 (S2). Thereby, the concave defects and the adherents on the obverse and the reverse surfaces of the object to be inspected 1 are simultaneously detected.

Figure 1C:
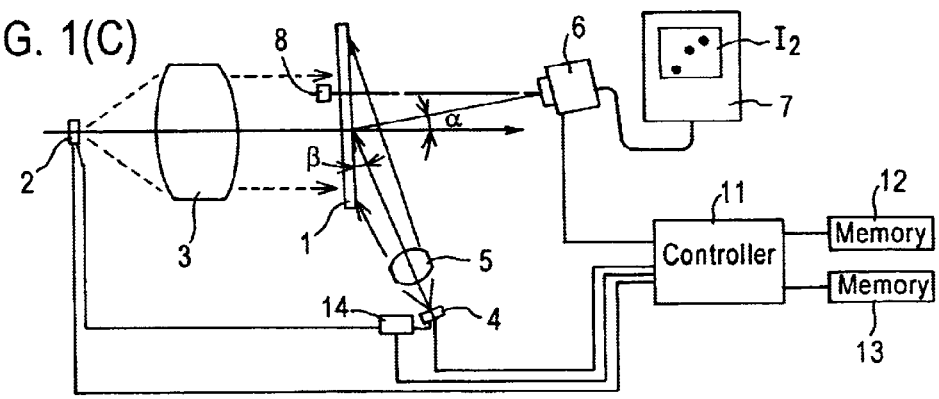

Then, as shown in FIG. 1C, when the controller 11 instructs the switch 14, which then turns off or blocks reflection light source 2, the object to be inspected 1 is illuminated at the low angle β by the reflection light source 4 (S3). The reflected scattered light irregularly reflected at the object to be inspected 1 is then detected by the detector 6 and then concurrently displayed on the monitor 7 (image $I_2$) and stored in memory 12, for example, a random access memory, of the controller 11 (S4). Thereby, only the adherents on the obverse surface of the object to be inspected 1 are detected.

Consequently, in the image $I_1$ displayed on the monitor 7 at the time of the inspection by use of the transmission light source 2, the positions of concave defects and adherents can be previously identified, and then, in the image $I_2$ displayed on the monitor 7 at the time of inspection by use of the reflection light source 4, which are adherents can be determined. This determination may either be made by visually comparing $I_1$ with $I_2$, or by comparing the images $I_1$ and $I_2$, that have been stored in memory 12 with a comparator in the controller 11 (S5).

Then, the object to be inspected 1 is reversed and the adherents on the reverse surface are detected in a like manner as described above, by use of the reflection light source 4. Lastly, by removing the adherents from the image $I_1$, either visually, or by means of the comparator in the controller 11, the concave defects can be discriminated.

For the images displayed on the monitor 7, after processing such as binarization and edge enhancement may be performed by use of controller 11, computing is performed to perform discrimination between the concave defects (S6) and the adherents (S7).

In the method according to this embodiment, of the defect ranks shown below, the defects of rank A could be detected.

| Rank | Pit, particle | Scratch (width) |
|---|---|---|
| A | 3 microns or less | 2 microns or less |
| B | 2 to 5 microns | 1 to 4 microns |
| C | 5 to 10 microns | 3 to 10 microns |
| D | 10 to 20 microns | 10 to 20 microns |
| E | 20 microns or more | 20 microns or more |

In the present invention, the angle of light incident on the object to be inspected 1 is important. It is desirable that the transmitted light be parallel light (collimated light). In this embodiment, the divergence of the transmission light source 2 can be adjusted within a range of ±10 degrees, preferably, ±5 degrees in the angle of light. In the case of the range of ±10 degrees, defects of rank B can be detected, and in the case of the range of ±5 degrees, defects of rank A can be detected. When the angle is larger than ±10 degrees, defects of rank C or lower can be detected. With respect to the reflected light, although the adherent detecting capability increases as the angle $\beta$ decreases, the illumination distribution in the illuminated part deteriorates if the angle $\beta$ is too small. Therefore, it is preferable to adjust the angle $\beta$ within a range of 4±3 degrees. When the angle $\beta$ is within this range, defects of rank B can be detected.

Although it is preferable that the transmission light source 2 be small in size, since the light quantity is insufficient if the size is too small, it is necessary for the transmission light source 2 to have a certain size. It is preferable that the aperture size be 8 mm or smaller. When the size is greater than this, light beams from various parts of the light source 2 are incident on the same part of the object to be inspected 1 at different angles and the directions of the scattered light beams are different, so that the resolution decreases. Moreover, when the light source 2 is too large, it is difficult to intercept the direct light from the light source 2. The apparent size of the light source 2 can be adjusted by inserting a pinhole, a diaphragm or the like in the optical system 3. As for the reflection light source 4, one that has a linear configuration as mentioned above is effective since light therefrom is obliquely incident. Since the angle P between the optical path of the linear light source 4 and the illuminated part of the object to be inspected 1 is small as mentioned above, the width of the linear light source is not necessarily large but may be small. As mentioned above, the width is approximately 1 mm in this embodiment.

While halogen lamps are used as the light sources 2 and 4 in the above-described embodiment, lasers may be used. For size reduction, the optical systems 3 and 5 may have an arrangement in which the optical path is bent by mirrors. As the transmission light source 2 and the reflection light source 4, a single light source in which the optical path is divided on the way into two paths for transmission and for reflection may be used instead of using two separate light sources. The light source configuration is not limited to a circular configuration or a linear configuration.

While in the above-described embodiment, the angle a between the detector 6 and the optical path is within the plane formed by the optical path of the transmission light source 2 and the optical path of the reflection light source 4 and opposite to the incidence direction of the reflection light source 4 with respect to the optical path of the transmission light source 2, the angle α may be set in any direction with respect to the optical path of the transmission light source 2.

When the transmitted light and the reflected light are both applied, illumination by the transmitted light is dominant, so that concave defects and adherents can be detected. Consequently, a similar measurement can be performed with a combination such that the reflection illumination is always on and only the transmission illumination is turned on and off.

Second Embodiment

FIG. 2 shows a second embodiment of an apparatus for visually inspecting a transparent or a translucent body according to the present invention. This visual inspection apparatus is substantially the same as the visual inspection apparatus of FIG. 1 except that a second reflection light source 9 and its optical system 10 are disposed on the reverse surface of the object to be inspected 1 so that the first reflection light source 4 and the optical system 5, and the second reflection light source 9 and the optical system 10 are symmetrical with respect to the object to be inspected 1. Therefore, corresponding parts are designated by the same reference numbers and will not be described.

Figure 4:
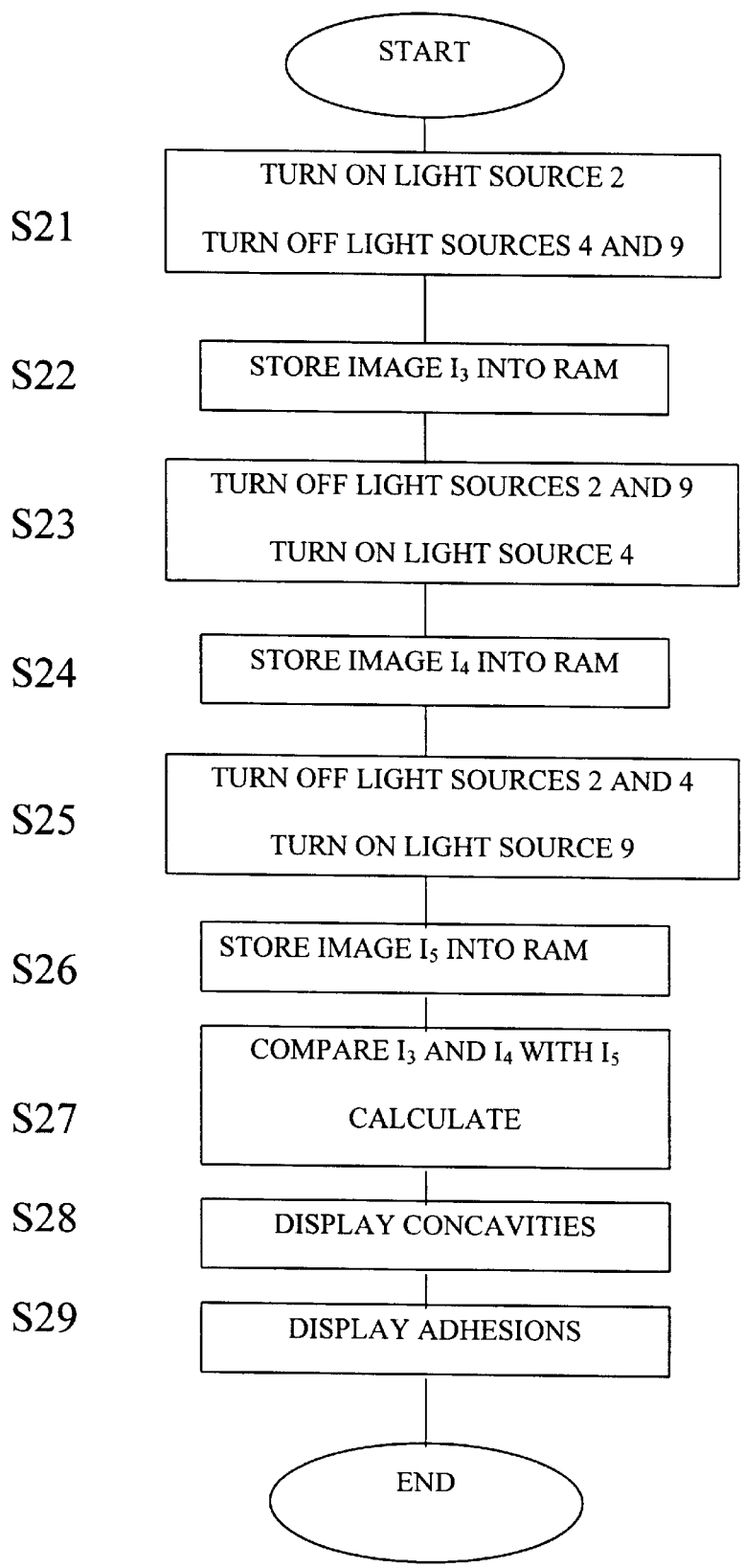
FIG. 4 is a method step diagram showing steps of operation of a second embodiment of an apparatus for visually inspecting a transparent or a translucent body according to the present invention.

Subsequently, a method of visually inspecting the object to be inspected 1 by using the visual inspection apparatus having the above-described structure will be described with reference to FIG. 2B, FIG. 2C, both with reference to FIG. 4. Here, a transparent glass substrate with a thickness of 1 mm is used as the object to be inspected 1, and concave defects and adherents thereof are detected so as to be distinguished from each other.

Figure 2A:
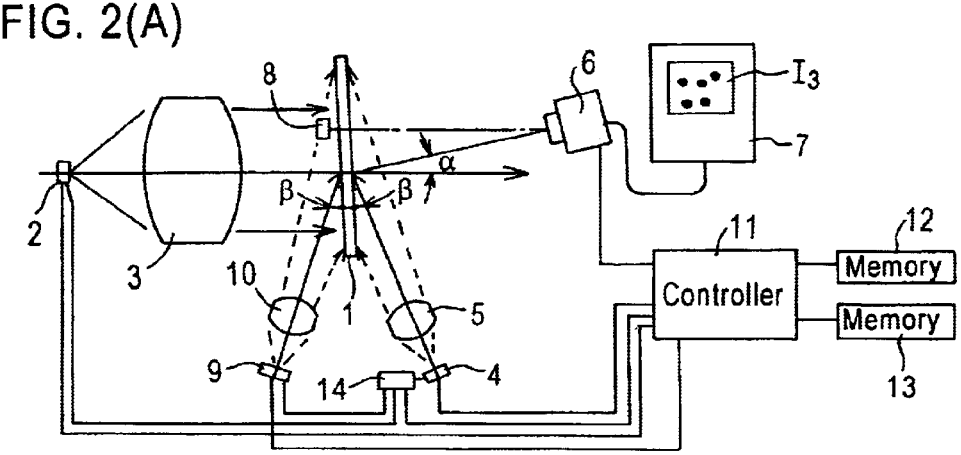
FIGS. 2A, 2B, and 2C are views showing a second embodiment of an apparatus for visually inspecting a transparent or a translucent body according to the present invention.

To perform a visual inspection of the object to be inspected 1 comprising a transparent glass substrate with a thickness of 1 mm by use of this visual inspection apparatus, first, as shown in FIG. 2A, when the controller 11 instructs the switch 14, which then turns off or blocks the first and the second reflection light sources 4 and 9, the object to be inspected 1 is illuminated by the transmission light source 2 (S21). Then, the transmitted light transmitted by the object to be inspected 1 is detected by the detector 6 and is concurrently displayed on the monitor 7 ($I_3$) and stored in memory 12, within the controller 11 (S22). Thereby, the concave defects and the adherents on the obverse and the reverse surfaces of the object to be inspected 1 are simultaneously detected.

Figure 2B:
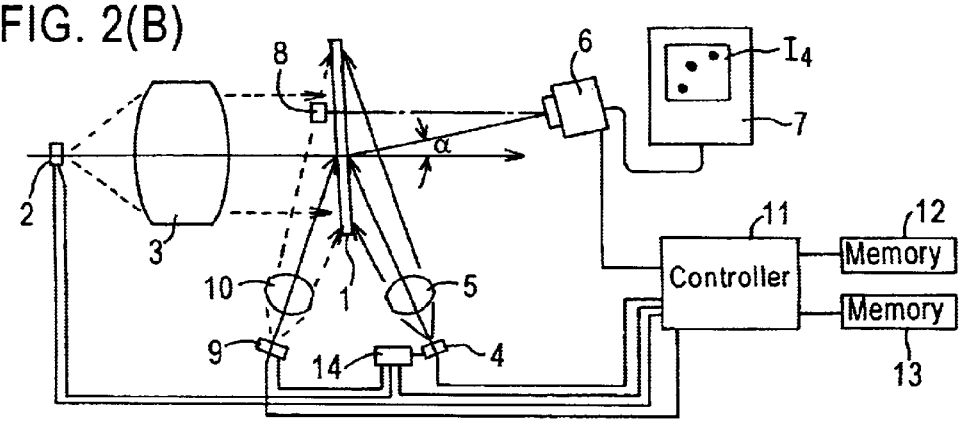

Then, as shown in FIG. 2B, when the controller 11 instructs the switch 14, which then turns off or blocks the transmission light source 2 and the second reflection light source 9, the object to be inspected 1 is illuminated by the reflected scattered light emitted from the first reflection light source 4 (S23). The reflected scattered light irregularly reflected at the object to be inspected 1 is then detected by the detector 6, and is then concurrently displayed on the monitor 7 ($I_4$) and stored in memory 12, within the controller 11 (S24). Thereby, only the adherents on the obverse surface of the object to be inspected 1 are detected.

Figure 2C:
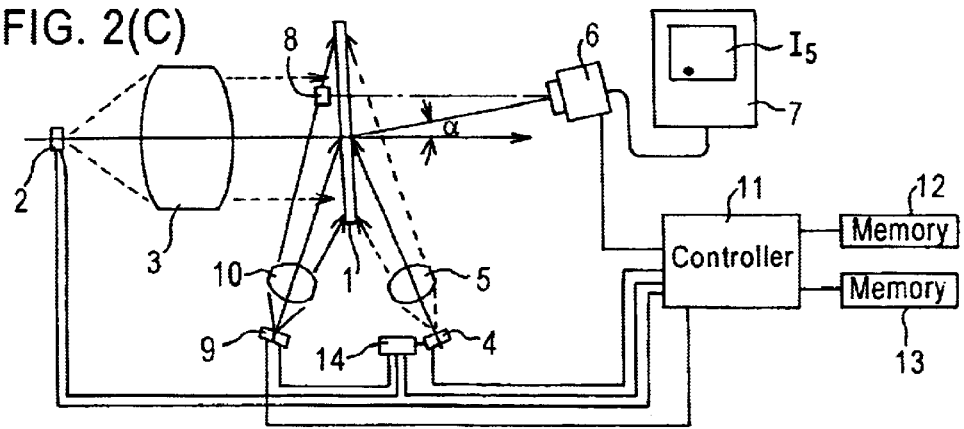

Lastly, as shown in FIG. 2C, when the controller 11 instructs the switch 14, which then turns off or blocks the transmission light source 2 and the first reflection light source 4, the object to be inspected 1 is illuminated by the reflected scattered light emitted from the second reflection light source 9 (S25). The reflected scattered light irregularly reflected at the object to be inspected 1 is detected by the detector 6 and is concurrently displayed on the monitor 7 ($I_5$) and stored in memory 12 within the controller 11 (S26). Thereby, only the adherents on the reverse surface of the object to be inspected 1 are detected.

Consequently, in the image $I_3$ displayed on the monitor 7 at the time of the inspection by use of the transmission light source 2, the positions of concave defects and adherents can be previously identified, and then, in the images $I_4$ and $I_5$ displayed on the monitor 7 at the times of the inspections by use of the first and the second reflection light sources 4 and 9, which are adherents on the obverse and the reverse surfaces can be determined. This determination may either be made by visually comparing both $I_4$ and $I_5$ with $I_6$, or by comparing both images $I_4$ and $I_5$ with $I_6$ that have been stored in memory 12 with a comparator in the controller 11 (S27). Then, by removing the adherents in the images $I_4$ and $I_5$ from the image $I_3$, either visually, or by means of the comparator in the controller 11, the concave defects can be discriminated.

For the images displayed on the monitor 7, like in the above-described first embodiment, after processing such as binarization and edge enhancement are performed by use of controller 11, computing is performed to perform discrimination between the concave defects (S28) and the adherents (S29).

In the second embodiment, since inspection of defects in the same area can be performed without the object to be inspected being turned from side to side, mapping of concave defects and adherents can be performed. In this embodiment, defects of rank A could be detected. Moreover, the adherents on both of the obverse and the reverse surfaces can simultaneously be detected by simultaneously applying the reflected light of both of the surfaces.

While a glass substrate is used as the object to be inspected 1 in the above-described embodiments, a translucent body such as plastic or resin may be used.

Advantages of the Present Invention

As is apparent from the description given above, according to the method of the above-described embodiments, since concave defects and adherents of the object to be inspected are detected by use of the transmitted light emitted from the transmission light source and transmitted by the object to be inspected and adherents of the object to be inspected are detected by use of the reflected scattered light emitted from the reflection light source and irregularly reflected at the object to be inspected, concave defects and adherents can be distinguished from each other and highly sensitive detection can be performed for both.

Moreover, according to the method of the embodiments, since the object to be inspected is illuminated with a combination of tuning on and off of the transmission light source and the reflection light source to separately perform the detection of concave defects and adherents by use of the transmission light source and the detection of adherents by use of the reflection light source, the detection of concave defects and adherents by use of the transmission light source and the detection of adherents by use of the reflection light source can more clearly be performed.

Moreover, according to the method of the embodiments, since the object to be inspected is turned from side to side to perform the detection of adherents by use of the reflection light source for both of the obverse and the reverse surfaces, the adherents on the obverse and the reverse surfaces can be distinguished from each other.

Moreover, according to the method of the embodiments, since the reflection light source is disposed on each of the obverse surface side and the reverse surface side of the object to be inspected and the object to be inspected is illuminated with a combination of turning on and off of the transmission light source and the two reflection light sources to separately perform the detection of concave defects and adherents by use of the transmission light source, the detection of adherents on the obverse surface by use of the first reflection light source and the detection of adherents on the reverse surface by use of the second reflection light source, the adherents on the obverse and the reverse surfaces can be distinguished from each other without the object to be inspected being turned from side to side.

According to the apparatus of the embodiments, since the detector is provided disposed on the obverse surface side of the object to be inspected in a position substantially parallel to the optical path of the transmission light source and where the light from the transmission light source is not directly incident, detecting concave defects and adherents of the object to be inspected by use of the transmitted light emitted from the transmission light source and transmitted by the object to be inspected, and detecting adherents of the object to be inspected by use of the reflected scattered light emitted from the reflection light source and irregularly reflected at the object to be inspected, concave defects and adherents can be inspected so as to be distinguished from each other.

Moreover, according to the apparatus of the embodiments, since the light intercepting plate for preventing the light from the transmission light source from being directly incident on the detector is disposed between the transmission light source and the object to be inspected or between the object to be inspected and the detector, the light from the transmission light source is not directly incident on the detector, so that the resolution improves.

Moreover, according to the apparatus of the embodiments, since the transmission light source is a light source in which the angles of light beams illuminating the object to be inspected are substantially the same, the scattered light can be made incident on the detector without any loss.

The foregoing description of the preferred embodiments of the invention have been presented for purposes of illustration and description. They are not intended to be exhaustive or to limit the invention to the precise forms disclosed, and obviously many modifications and variations are possible in light of the above teaching. The illustrated embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method of visually inspecting an object having a transparent body or a translucent body, wherein light is applied to a reverse surface of an object to be inspected by a transmission light source, wherein light is applied to, at a low angle, to at least one of an obverse surface and the reverse surface of the object to be inspected by a reflection light source, wherein detection of concave defects and adherents of the object to be inspected by use of transmitted light emitted from the transmission light source and transmitted by the object to be inspected and detection of adherents of the object to be inspected by use of reflected scattered light emitted from the reflection light source and irregularly reflected at the object to be inspected are performed by a detector disposed on an obverse surface side of the object to be inspected in a position substantially parallel to an optical path of the transmission light source and where light from the transmission light source is not directly incident, and wherein the detected results are compared to distinguish the concave defects and the adherents.

2. A method of visually inspecting an object having a transparent body or a translucent body as claimed in claim 1,
wherein the concave defects and the adherents of the object to be inspected are distinguished from each other by illuminating the object to be inspected with a combination of turning on and off of the transmission light source and the reflection light source and separately performing the detection of the concave defects and the adherents by use of the transmission light source and the detection of the adherents by use of the reflection light source.

3. A method of visually inspecting an object having a transparent body or a translucent body as claimed in claim 2,
wherein the object to be inspected is turned from side to side to perform the detection of the adherents by use of the reflection light source for both of the obverse and the reverse surfaces.

4. A method of visually inspecting an object having a transparent body or a translucent body as claimed in claim 1,
wherein the reflection light source is disposed on each of the obverse surface side and the reverse surface side of the object to be inspected, and the concave defects and the adherents of the object to be inspected are distinguished from each other by illuminating the object to be inspected with a combination of turning on and off of the transmission light source and the two reflection light sources and separately performing the detection of the concave defects and the adherents by use of the transmission light source, detection of adherents on the obverse surface by use of the first reflection light source and detection of adherents on the reverse surface by use of the second reflection light source.

5. An apparatus for visually inspecting an object having a transparent body or a translucent body, comprising:
a transmission light source disposed on a reverse surface side of an object to be inspected and applying light to a reverse surface of the object to be inspected;
a reflection light source disposed on at least one of an obverse surface side and the reverse surface side of the object to be inspected and applying light to the object to be inspected at a low angle;
a detector disposed on the obverse surface side of the object to be inspected in a position substantially parallel to an optical path of the transmission light source and where the light from the transmission light source is not directly incident; and
a controller for controlling said detector to detect concave defects and adherents of the object to be inspected by use of transmitted light emitted from the transmission light source and transmitted by the object to be inspected, for controlling said detector to detect adherents of the object to be inspected by use of reflected scattered light emitted from the reflection light source and irregularly reflected at the object to be inspected, and for distinguishing the concave defects and the adherents by comparing the detected results.

6. An apparatus for visually inspecting an object having a transparent body or a translucent body as claimed in claim 5,
wherein an angle of inclination of the detector from the optical path of the transmission light source is 5±3 degrees.

7. An apparatus for visually inspecting an object having a transparent body or a translucent body as claimed in claim 5,
wherein an angle of incidence of the reflection light source on the object to be inspected is approximately 4±3 degrees.

8. An apparatus for visually inspecting an object having a transparent body or a translucent body as claimed in claim 5,
wherein a light intercepting plate for preventing the light from the transmission light source from being directly incident on the detector is disposed between the transmission light source and the object to be inspected or between the object to be inspected and the detector.

9. An apparatus for visually inspecting an object having a transparent body or a translucent body as claimed in claim 5,
wherein the transmission light source is a light source in which angles of light beams illuminating the object to be inspected are substantially the same.

10. An apparatus for visually inspecting an object having a transparent body or a translucent body as claimed in claim 6,
wherein an angle of incidence of the reflection on the object to be inspected is approximately 4±3 degrees.

11. An apparatus for visually inspecting an object having a transparent body or a translucent body as claimed in claim 6,
wherein a light intercepting plate for preventing the light from the transmission light source from being directly incident on the detector is disposed between the transmission light source and the object to be inspected or between the object to be inspected and the detector.

12. An apparatus for visually inspecting an object having a transparent body or a translucent body as claimed in claim 6,
wherein the transmission light source is a light source in which angles of light beams illuminating the object to be inspected are substantially the same.

13. An apparatus for visually inspecting an object having a transparent body or a translucent body, comprising:
a transmission light source disposed on a reverse surface side of an object to be inspected and applying light to a reverse surface of the object to be inspected;
a reflection light source disposed on at least one of an obverse surface side and the reverse surface side of the object to be inspected and applying light to the object to be inspected at a low angle; and
a detector disposed on the obverse surface side of the object to be inspected in a position substantially parallel to an optical path of the transmission light source and where the light from the transmission light source is not directly incident; and
a controller for controlling said detector to detect concave defects and adherents of the object to be inspected by use of transmitted light emitted from the transmission light source and transmitted by the object to be inspected, for controlling said detector to detect adherents of the object to be inspected by use of reflected scattered light emitted from the reflection light source and irregularly reflected at the object to be inspected, and for distinguishing the concave defects and the adherents by comparing the detected results,
wherein an angle of inclination of the detector from the optical path of the transmission light source is approximately 5±3 degrees, wherein an angle of incidence of the reflection light source on the object to be inspected is approximately 4±3 degrees, and wherein the transmission light source is a light source in which angles of light beams illuminating the object to be inspected are substantially the same.

14. A method for visually inspecting an object having a transparent body or a translucent body, comprising the steps of:

(a) illuminating said object with a first light source applied to a reverse surface of said object;

(b) detecting, under the illuminating condition of the step (a), a first image of said object with a detector;

(c) storing said first image of said illuminated object into a memory;

(d) illuminating said object with only a second light source applied to at least one of a obverse surface and the reverse surface of said object;

(e) detecting, under the illuminating condition of the step (d), a second image of said illuminated object with a detector;

(f) storing said second image of said illuminated object into a memory;

(g) comparing said first stored image and second stored image to distinguish concave defects and adherents, wherein light from said second light source is applied at a low angle to illuminate said transparent body.

15. The method for visually inspecting an object having a transparent body or a translucent body as claimed in claim 14, wherein said first image of said illuminated transparent body includes concavities in said transparent body.

16. The method for visually inspecting an object having a transparent body or a translucent body as claimed in claim 14, wherein, said second image of said illuminated transparent body includes adhesions on said transparent body.

17. The method for visually inspecting an object having a transparent body or a translucent body as claimed in claim 15, wherein said second image of said illuminated transparent body includes adhesions on said transparent body.

18. A method of visually inspecting both of a front surface and a rear surface of an object that has a transparent body or a translucent body, wherein light is illuminated, at a first angle, to the rear surface of the object by a transmission light source, wherein lights are separately illuminated, at a second angle lower than the first angle, to the front surface and the rear surface of the object by at least one reflection light source, and wherein detection of concave defects and adherents of the object by use of transmitted light emitted from the transmission light source and transmitted by the object and detection of adherents of the object by use of scattered lights separately emitted from the at least one reflection light source and irregularly reflected on the front surface and the rear surface are performed by a detector.

19. A method as claimed in claim 18, wherein the object is turned from side to side to carry out the separate light illumination.

20. A method as claimed in claim 18, reflection light sources are respectively disposed on a front surface side and a rear surface side of the object, and the lightings of the reflection light sources are individually controlled to carry out the separate light illumination.

* * * * *